United States Patent
Lele et al.

(10) Patent No.: US 7,018,655 B2
(45) Date of Patent: Mar. 28, 2006

(54) AMPHIPHILIC DIBLOCK, TRIBLOCK AND STAR-BLOCK COPOLYMERS AND THEIR PHARMACEUTICAL COMPOSITIONS

(75) Inventors: Bhalchandra Shripad Lele, Pune (IN); Jean-Christophe Leroux, Montréal (CA)

(73) Assignee: Labopharm, Inc., Quebec (CA)

( * ) Notice: Subject to any disclaimer, the term of this patent is extended or adjusted under 35 U.S.C. 154(b) by 340 days.

(21) Appl. No.: 10/101,093

(22) Filed: Mar. 18, 2002

(65) Prior Publication Data

US 2003/0181613 A1    Sep. 25, 2003

(51) Int. Cl.
*A61K 9/14* (2006.01)
*A61K 9/127* (2006.01)
*A61K 47/30* (2006.01)

(52) U.S. Cl. .............. 424/486; 424/450; 514/772.3
(58) Field of Classification Search ............... 424/486, 424/489, 450; 514/772.3; 526/222
See application file for complete search history.

(56) References Cited

U.S. PATENT DOCUMENTS

| | | | | |
|---|---|---|---|---|
| 4,699,950 A | * | 10/1987 | Sato et al. | 525/185 |
| 5,891,468 A | * | 4/1999 | Martin et al. | 424/450 |
| 6,060,518 A | | 5/2000 | Kabanov et al. | |
| 6,201,065 B1 | | 3/2001 | Pathak et al. | |
| 6,284,267 B1 | | 9/2001 | Aneja | |
| 6,322,805 B1 | | 11/2001 | Kim et al. | |
| 6,338,859 B1 | * | 1/2002 | Leroux et al. | 424/489 |

OTHER PUBLICATIONS

Jones et al., "Polymeric micelles-a new generation of colloidal drug carriers", European Journal of Pharmaceutics and Biopharmasceutics, 48 (1999) pp. 101-111.
Zhang et al., "Development of amphiphilic diblock copolymers as micellar carriers of taxol", International Journal of Pharmaceutics, 132 (1996) pp. 195-206.
Kataoka et al., "Block copolymer micelles for drug delivery: design, characterization and biological significance", Advanced Drug Delivery Reviews 47 (2001) pp. 113-131.

* cited by examiner

*Primary Examiner*—Thurman K. Page
*Assistant Examiner*—Blessing Fubara
(74) *Attorney, Agent, or Firm*—McHale & Slavin, P.A.

(57) ABSTRACT

This invention relates to novel amphiphilic diblock, triblock copolymers and star-shaped block copolymers comprising a biodegradable polymer covalently attached at the polymer ends, to a hydrophilic vinyl polymer, via divalent sulfur atom; to a process for producing the block polymers; to a polymerization process which comprises subjecting the monomers capable of radical polymerization to radical polymerization in the presence of a macromolecular biodegradable chain-transfer agent; and to pharmaceutical compositions comprising the block copolymers loaded with therapeutic agents.

8 Claims, No Drawings

AMPHIPHILIC DIBLOCK, TRIBLOCK AND STAR-BLOCK COPOLYMERS AND THEIR PHARMACEUTICAL COMPOSITIONS

FIELD OF THE INVENTION

This invention relates to novel amphiphilic diblock, triblock and star-shaped block copolymers comprising a biodegradable polymer covalently attached at the polymer ends, to a hydrophilic vinyl polymer, via divalent sulfur atom; to a process for producing the block polymers; to a polymerization process which comprises subjecting the monomers capable of radical polymerization to radical polymerization in the presence of a macromolecular biodegradable chain-transfer agent; and to pharmaceutical compositions comprising the block copolymers loaded with therapeutic agents.

BACKGROUND OF THE INVENTION

Block copolymers, which comprise hydrophilic and hydrophobic polymers covalently bound to one another, are, by definition, amphiphilic polymers. Above a certain concentration, called the critical micellar concentration (CMC) or critical aggregation concentration (CAC), the block copolymers can self-assemble to form supramolecular aggregates (micelles or nanoparticles) in aqueous medium. The micelles consist of two distinct regions—an interior region of hydrophobic polymer chains (the core region), which has the ability to solubilize hydrophobic molecules; and an outer region of well-solvated hydrophilic polymer chains (the shell region), which imparts colloidal stability. Block copolymers can be designed to exhibit low CAC (few milligrams per liter) and high thermodynamic stability, compared to low molecular weight surfactants. Generally, the size of block copolymer micelles is of the order of 10–40 nanometers (Reiss, G.; Hurtrez, G.; Bahadur, P. Block Copolymers. 1985, In *Encyclopedia of Polymer Science and Engineering*; Korschwitz, J. I. Ed.; Wiley-Interscience: N.Y.). Due to these properties, block copolymer micelles comprising hydrophilic-biocompatible and hydrophobic biodegradable segments have attracted considerable attention related to their use as nanosized carriers of poorly water-soluble drugs. These micelles can facilitate the solubilization of poorly water-soluble drugs, increase their circulation time in vivo and eventually target them passively or actively by means of targeting ligands to specific tissues (e.g. tumoral tissues) (Kataoka, K.; Harada, A.; Nagasaki, Y. 2001, *Adv. Drug Deliv. Rev.* 47, 113–131; Torchilin, V. P. 2001, *J. Controlled Rel.* 73, 137–172; Jones, M.-C.; Leroux, J.-C. 1999, *Eur. J. Pharm. Biopharm.* 48, 101–111.).

DESCRIPTION OF THE PRIOR ART

Block copolymers having a variety of architectures, e.g. A-B, A-B-A and star-shaped block copolymers are known in the art. Among A-B type diblock copolymers, monomethoxy poly(ethylene glycol)-block-poly(D,L-lactide) (MPEG-b-PDLLA) (Yasugi, K.; Nagasaki, Y.; Kato, M.; Kataoka, K. 1999, *J. Controlled Rel.* 62, 89–100); monomethoxy poly(ethylene glycol)-block-poly($\epsilon$-caprolactone) (MPEG-b-PCL) (Shin, I. G.; Kim, S. Y.; Lee, Y. M., Cho, C. S.; Sung, Y. K. 1998, *J. Controlled Rel.* 51, 1–11) and monomethoxy poly(ethylene glycol)-block-poly($\beta$ benzyl L-aspartate) (MPEG-b-PBLA) (Yokoyama, M.; Miyauchi, M.; Yamada, N.; Okano, T.; Sakurai, Y.; Kataoka, K.; Lnoue, S. 1990, *J. Controlled Rel.* 11, 269–278) have been extensively studied for micellar drug delivery. MPEG-b-PDLLA has been synthesized by ring opening polymerization of D,L-lactide initiated either with potassium monomethoxy poly(ethylene glyco)late at 25° C. in tetrahydrofuran (THF) (Jeong, B.; Bae, Y. H.; Lee, D. S.; Kim, S. W. 1997, *Nature* 388, 860–862) or with MPEG at 110 to 150° C. in the bulk (Kim, S. Y.; Shin, I. G.; Lee, Y. M. 1998, *J. Controlled Rel.* 56, 197–208). Similarly, MPEG-b-PCL has also been synthesized by ring opening polymerization of $\epsilon$-caprolactone initiated with potassium MPEG alcoholate in THF at 25° C.(Deng, X. M.; Zhu, Z. X.; Xiong, C. D.; Zhang, L. L. 1997, *J. Polym. Sci. Polym. Chem. Ed.* 35, 703–708) or with MPEG at 140 to 180° C. in the bulk (Cerrai, P.; Tricoli, M.; Andruzzi, F.; Poci, M.; Pasi, M. 1989, *Polymer* 30, 338–343). MPEG-b-PBLA was synthesized by polymerization of N-carboxyanhydride of aspartic acid initiated with MPEG amine, in a solvent at 25° C. (Yokoyama, M.; Lnoue, S.; Kataoka, K.; Yui, N.; Sakurai, Y. 1987, *Makromol. Chem. Rapid Commun.* 8, 431–435).

Among the different drug molecules that have been loaded in diblock copolymer micelles, are paclitaxel (Zhang, X.; Jackson, J. K.; Burt, H. M. 1996, *Int. J. Pharm.* 132, 195–206); testosterone (Allen, C.; Eisenberg, A.; Mrsic, J.; Maysinger, D. 2000, *Drug Deliv.* 7, 139–145); indomethacin (Kim, S. Y.,; Shin, I. G.; Lee, Y. M.; Cho, C. S.; Sung, Y. K. 1998, *J. Controlled Rel.* 51, 13–22); FK 506, L-685, 818 (Allen, C.; Yu, Y.; Maysinger, D.; Eisenberg, A. 1998, *Bioconjug. Chem.* 9, 564–572); dihydrotestosterone (Allen, C.; Han, J.; Yu, Y.; Maysinger, D.; Eisenberg, A. 2000, *J. Controlled Rel.* 63, 275–286); amphotericin B (Kwon, G. S.; Naito, M.; Yokoyama, M.; Okano, T.; Sakurai, Y.; Kataoka, Y. 1998, *J. Controlled Rel.* 51, 169–178); doxorubicin (Yu, B. G.; Okano, T.; Kataoka, K.; Kwon, G. 1998, *J. Controlled Rel.* 53, 131–136) and KRN (Yokoyama, M.; Satoh, A.; Sakurai, Y.; Okano, T.; Matsumara, Y.; Kakizoe, T.; Kataoka, K. 1998, *J. Controlled Rel.* 55, 219–229). In some cases, the incorporation of drugs into polymeric micelles has resulted in increased efficacy or decreased side-effects.

Among A-B-A type triblock copolymer compositions, poly(ethylene oxide)-block-poly(propylene oxide)-block-poly(ethylene oxide) based drug-loaded micelles have received extensive study (Kabanov, A. V. et al., 1989, *FEBS Lett.* 258, 343–345; Batrakova, E. V. et al 1996, *Br. J. Cancer* 74, 1545–1552; Batrakova, E. V.; Han, H. Y.; Alakhov, V. Y.; Miller, D. W.; Kabanov, A. V. 1998, *Pharm. Res.* 15 850–855; Rapoport, N.Y.; Marin, A.; Luo, Y.; Prestwich, G. D.; Muniruzzaman, M. J. 2002, *Pharm. Sci.* 91, 157–170; Rapport, N.Y., Herron, J. N.; Pitt, W. G.; Pitina, L. 1999, *J. Controlled Rel.* 58, 153–162; Cheng, H. Y.; Holl, W. W. 1990, *J. Pharm. Sci.* 79, 907–912). However, these polymers do not constitute a biodegradable embodiment. In an effort to develop such an embodiment, researchers have developed various biodegradable, amphiphilic A-B-A triblock copolymers.

Ma et al (2001) reported synthesis of PDLLA-b-PEG-b-PDLLA by ring opening polymerization of D,L-lactide initiated with PEG at 180° C. in the bulk using stannous 2-ethyl hexanoate as catalyst (Ma, J.; Feng, P.; Ye, C.; Wang, Y.; Fan, Y. 2001, *Colloid Polym. Sci.* 279, 387–392). Zhu et al (1999) synthesized PDLLA-b-PEG-b-PDLLA by anionic ring opening polymerization of D,L-lactide initiated with potassium poly(ethylene glyco)late (Zhu, Z.; Xiong, C.; Zhang, L.; Yuan, M.; Deng, X. 1999, *Eur. Polym. J.* 35, 1821–1828). Multiblock poly(ethylene glycol)-block-poly(D,L-lactide-co-glycolide) (PEG-b-PLGA) was reported by Ferruti et al (1995), wherein PEG was reacted with phosgene followed by polycondensation of the resulting $\alpha,\omega$-bis(chloroformate) with PLGA oligomers in chloroform at room temperature (Ferruti, P.; Penco, M.; Dàddato, P.; Ranucci, E.; Deghenghi, R. 1995, *Biomaterials* 16, 1423–1428). Li and Kissel (1993) reported synthesis of triblock PLGA-b-PEG-b-PLGA by first forming a complex between PEG and aluminum triisopropoxide and then initiating the ring opening polymerization of lactide/glycolide with PEG-Aluminum isopropoxide complex at 110° C. (Li, Y. X.; Kissel, T. 1993, *J. Controlled Rel.* 27, 247–257). PCL-b-PEG-b-PCL and PLA-b-PEG-b-PLA have also been synthesized by ring opening polymerization of ε-caprolactone and L-lactide, initiated with PEG in the absence of a catalyst at 185° C. and 140° C., respectively. (Guerra, G. D.; Cerrai, P.; Tricoli, M.; Maltinti, S.; *J. Biomater. Sci. Mater. Medicine* 12, 313–317).

An additional class of block copolymers, thought to be useful as drug carriers, has recently emerged, and are classified as star-shaped amphiphilic block copolymers. These polymers have a well-defined architecture characterized by a large number of arms that emerge from the central core and comprise hydrophobic and hydrophilic macromolecules covalently attached at one point. Star block copolymers have very low critical micellar concentration and act as intrinsically stable polymeric micelles capable of solubilizing poorly water-soluble drugs see e.g. U.S. Pat. No. 6,284,267. Li and Kissel (1998) reported synthesis of four and eight arm star shaped PEO-b-PLA, PEO-b-PLGA and PEO-b-PCL by PEO initiated ring-opening polymerization of L-lactide, lactide/glycolide and ε-caprolactone, respectively; in toluene, using triethylaluminum as catalyst (Li, Y.; Kissel, T. *Polymer* 39, 4421–4427). Choi et al (1998) synthesized star-shaped PEO-b-PLA and PEO-b-PCL by four arm PEO initiated ring opening polymerization of lactide and ε-caprolactone, respectively; at 110° C. in the bulk, using stannous 2-ethyl hexanoate as the catalyst. (Choi, Y. K.; Bae, Y. H.; Kim, S. W. 1998, *Macromolecules* 31, 8766–8774). Hedrick et al (1998) reported combination of ring opening and atom transfer radical polymerization (ATRP). These authors synthesized dendrimer like multiarm poly(ε-caprolactone)-2-bromoisobutyrate which was used as macroinitiator in ATRP of 2-hydroxyethyl methacrylate and PEG-methacrylate, respectively. (Hedrick, J. L.; Trollsas, M.; Hawker, C. J.; Atthoff, B.; Claesson, H.; Heise, A.; Miller, R. D.; Mecerreyes, D.; Jerome, R.; Dubois, Ph. 1998, *Macromolecules* 31, 8691–8705).

U.S. Pat. No. 6,322,805 relates to biodegradable polymeric micelles capable of solubilizing a hydrophobic drug in a hydrophilic environment comprising an amphiphilic block copolymer having a hydrophilic poly(alkylene oxide) component and a biodegradable hydrophobic polymer selected from the group consisting of poly(lactic acid), poly(glycolic acid), poly(lactic-co-glycolic acid), poly(ε-caprolactone) and derivatives and mixtures thereof. The patent broadly teaches A-B-A type triblock copolymers which may contain poly(ε-caprolactone) as one of their constituents, but fails to disclose the particular hydrophilic vinyl polymers comprising block copolymers set forth in the instant invention, nor a method by which such polymers could be successfully synthesized.

U.S. Pat. No. 6,201,065 is directed toward gel-forming macromers including at least four polymer blocks including at least two hydrophilic groups, one hydrophobic group and one crosslinkable group. The reference discloses the possible utilization of a plurality of polymerization techniques, among which is included attachment of a thiol to a reactant and subsequent covalent attachment to a macromer. The reference further teaches the formation of biodegradable links separating the cross-linking reactive groups. The reference fails to teach or suggest the particular type of block copolymers set forth in the instant invention, nor a method by which such polymers could be successfully synthesized.

Most of the reports cited above show that PEG has been the preferred choice of hydrophilic segment that imparts colloidal stability for block copolymer micelles. However, under certain conditions, PEG can promote the aggregation of nanoparticles after freeze-drying (De Jaghere, F.; Alleman, E.; Leroux, J.-C.; Stevels, W.; Feijen, J.; Doelker, E.; Gurny, R. 1999, *Pharm. Res.* 16, 859–866). Moreover, PEG chains are devoid of pendant sites that could be used to conjugate various functional groups for targeting or to induce pH and/or temperature sensitivity to the micelles. Hydrophilic polymers synthesized by polymerization or copolymerization of various vinyl monomers can provide such properties to the block copolymers. Examples of such block copolymers include poly(N-isopropylacrylamide)-block-poly(L-lactic acid) (Kim, I-S.; Jeong, Y-I.; Cho, C-S.; Kim, S-H. 2000, *Int. J. Pharm.* 211, 1–8); poly(N-isopropylacrylamide)-block-poly(butyl methacrylate) (Chung, J. E.; Yooyama, M.; Yamato, M.; Aoyagi, T.; Sakurai, Y., Okano, T. 1999, *J. Controlled Rel.* 62, 115–127); poly(N-isopropylacrylamide-co-methacrylic acid-co-octadecyl acrylate) (Taillefer, J.; Jones, M-C.; Brasseur, N.; Van Lier, J. E.; Leroux, J-C. 2000, *J. Pharm. Sci.* 89, 52–62). Moreover, structural variation of outer hydrophilic shells to produce micelles that can interact with many different biological environments is highly desirable.

Recently, Benhamed et al (2001) reported novel poly(N-vinylpyrrolidone)-block-poly(D,L-lactide) (PVP-b-PDLLA) micelles (Benhamed, A.; Ranger, M.; Leroux, J.-C. 2001, *Pharm. Res.* 18, 323–328). These micelles have potential advantage of the PVP shell being both lyoprotectant and cryoprotectant (Townsend, M.; Deluca, P. P. 1988, *J. Parent. Sci. Technol.* 37, 190–199; Doebbler, G. F. 1966, *Cryobiology* 3, 2–11). Also PVP, owing to its amphiphilic nature is capable of interacting with a variety of compounds (Garrett, Q.; Milthorpe, B. K. 1996, *Invest. Ophthalmol.* 37, 2594–2602; Alencar de Queiro, A. A.; Gallordo, A.; Romman, J. S. 2000, *Biomaterials* 21, 1631–1643). On the other hand, the group of Jeong et al (1999),(2000), reported the use of poly(2-ethyl-2-oxazoline) (PEtOz) as the shell-forming polymer in poly(2-ethyl-2-oxazoline)-block-poly(D,L-lactide) (PEtOz-b-PDLLA), poly(2-ethyl-2-oxazoline)-block-poly(ε-caprolactone) (PEtOz-b-PCL), and poly(2-ethyl-2-oxazoline)-block-poly(1,3 trimethylene carbonate) (PEtOz-b-PTMC). The hydrophilic shells in the above-described micelles form hydrogen-bonding complexes with poly(acrylic acid) that can dissociate above pH 3.9. (Lee, S. C.; Chang, Y.; Yoon, J.-S.; Kim, C.; Kwon, I. C.; Kim, Y-H; Jeong, S. Y. 1999, *Macromolecules* 32, 1847–1852; Kim, C.; Lee, S. C.; Shin, J. H.; Kwon, I. C.; Jeong, S. Y. 2000, *Macromolecules* 33, 7448–7452).

Poly(N-(2-hydroxypropyl)methacrylamide) (PHPMA) is another hydrophilic, non-immunogenic and biocompatible polymer. It has been demonstrated that anticancer drugs conjugated to PHPMA can exhibit stronger antitumor effects than the free drugs. Indeed, PK1 and PK2 are doxorubicin-conjugated PHPMA prodrugs that are now in clinical trials (Kopecek, J.; Kopecova, P.; Minko, T.; Lu, Z-R. 2000, *Eur. J. Pharm. Biopharm.* 50, 61–81). Free PHPMA has also been used as one of the components of poloxamer micelle-based chemotherapy liquid composition (Kabanov, A. V.; Alakhov, V. Y. 2000, U.S. Pat. No. 6,060,518). Moreover, block and graft copolymers of PHPMA with poly(L-lysine) and poly(trimethylaminoethylmethacrylate) have been described for gene delivery applications (Toncheva, V.; Wolfert, M. A.; Dash, P. R.; Oupicky, D.; Ulbrich, K.;

Seymour, L. W.; Schacht, E. H. 1998, *Biochim. Biophys. Acta.* 1380, 354–368; Konack, C.; Mrkvickova, L.; Nazarova, O.; Ulbrich, K.; Seymour, L. W. 1998, *Supramol. Sci.* 5, 67–74).

In view of these results, amphiphilic block copolymer micelles based on PHPMA and biodegradable polymers would be desirable. Diblock copolymers of PHPMA with poly(N-isopropylacrylamide) and poly(butyl methacrylate) have been reported (Konack, C.; Oupicky, D.; Chytry, V.; Ulbrich, K. 2000, *Macromolecules* 33, 5318–5320; Teodorescu M.; Matyjaszewski, K. 1999, *Macromolecules* 32, 4826–4831). PHPMA comprising block copolymers (except PHPMA-block-poly(butylmethacrylate) have been synthesized by conjugation reaction between carboxyl and amine functionalized polymers. Generally, this procedure often leads to poor conjugation yields, and the elimination of unreacted polymers is not trivial (Chung, J. E.; Yokoyama, M.; Yamato, M.; Aoyagi, T.; Sakurai, Y.; Okano, T. 1999, *J. Controlled Rel.* 62, 115–127). PHPMA-block-poly(butyl methacrylate) was synthesized by ATRP of HPMA monomer initiated with poly(butyl methacrylate) macroinitiator. However, this procedure gave poor yields and uncontrolled polymerization (large polydispersity) due to the competition of PHPMA amide nitrogen atom with the added ligands, for Cu (I) catalyst used in ATRP (Teodorescu M.; Matyjaszewski, K. 1999, *Macromolecules* 32, 4826–4831). Moreover, PHPMA is insoluble in THF, the solvent suitable for polymer-initiated anionic ring-opening polymerization of lactide, glycolide and ε-caprolactone. In addition, at high temperatures, the reactivity of secondary hydroxyl groups in the PHPMA pendant chain should not be neglected. Indeed, Breitenbach and Kissel (1998) reported grafting of PDLLA and poly(D,L-lactide-co-glycolide) chains onto poly(vinyl alcohol) (PVA) under melt polymerization conditions via PVA-initiated ring-opening polymerization of D,L-lactide and glycolide (Breitenbach, A.; Kissel, T. 1998, *Polymer* 39, 3261–3271).

The synthesis of block copolymers composed of hydrophobic biodegradable polymers and hydrophilic vinyl polymers has been previously reported by Hedrick et al (Hedrick, J. L.; Trollsas, M.; Hawker, C. J.; Atthoff, B.; Claesson, H.; Heise, A.; Miller, R. D.; Mecerreyes, D.; Jerome, R.; Dubois, Ph. 1998, *Macromolecules* 31, 8691–8705). However, in this study the authors used atom transfer radical polymerization (ATRP) to prepare the copolymers. Unfortunately, ATRP is not optimal for the polymerization of many vinyl monomers (e.g. HPMA, VP). The present inventors therefore decided to radically polymerize hydrophilic vinyl monomer in the presence of macromolecular biodegradable chain transfer-agent and obtain the block copolymers thereof. In the prior art, Sato et al (1987) synthesized a variety of A-B and A-B-A type block copolymers by free radical polymerization of vinyl monomers, such as vinyl acetate, methyl methacrylate, N,N-dimethylacrylamide and acrylic acid, in the presence of mono or dithiol-terminated PEG, poly(propylene glycol), poly(methyl methacrylate), poly(vinyl alcohol) and poly(styrene) as chain-transfer agents (Sato, T.; Yamauchi, J.; Okaya, T. 1987, U.S. Pat. No. 4,699,950). Inoue et al (1998) synthesized A-B type block copolymer micelles by radical polymerization of acrylic acid in the presence of thiol-terminated oligo(methyl methacrylate) as chain-transfer agent (Inoue, T.; Chen, G.; Nakame, K.; Hoffman, A. S. 1998, *J. Controlled Rel.* 51, 221–229). However, prior artisans failed to teach or suggest the use of macromolecular biodegradable chain-transfer agent.

SUMMARY OF THE INVENTION

This invention provides amphiphilic diblock, triblock and star-shaped block copolymers of a hydrophobic biodegradable polyester (e.g. poly(ε-caprolactone)(PCL), poly(D,L-lactic acid) (PDLLA)) with a hydrophilic vinyl polymer (e.g. poly(N-(2-hydroxypropyl)methacrylamide) (PHPMA) and poly(N-vinylpyrrolidone), synthesized by the process of the instant invention, which comprises radically polymerizing respective vinyl monomers in the presence of a chain-transfer agent derived from the polyester. The present invention further provides polymeric micelle compositions of the block copolymers physically loaded with therapeutic agents.

It is therefore an objective of the instant invention to describe the preparation of amphiphilic diblock, triblock and star-shaped block copolymers comprising hydrophilic vinyl segments and biodegradable segments.

It is a further objective of the instant invention to teach a polymerization process which employs macromolecular biodegradable chain-transfer agents for the preparation of such polymers.

It is yet another objective of the instant invention to provide pharmaceutical compositions of the block copolymers physically loaded with therapeutic agents.

DETAILED DESCRIPTION OF THE INVENTION

Accordingly, the present invention provides amphiphilic diblock, triblock and star-shaped block copolymers comprising a biodegradable polymer, covalently attached at the polymer ends, to hydrophilic vinyl polymers via divalent sulfur atom. The instant invention further teaches a process for the preparation of said block copolymers which comprises radically polymerizing vinyl monomers in the presence of a macromolecular biodegradable chain-transfer agent; and is further directed towards pharmaceutical compositions of the block copolymers physically loaded with therapeutic agents. The following embodiments delineate various groupings containing illustrative, but non-limiting embodiments, of the instant invention.

In one embodiment, the biodegradable polymer may include at least one member which is selected from a group consisting of a poly(ester), a poly(amide), a poly(ester-amide), a poly(anhydride) and combinations thereof.

In an alternative embodiment, the biodegradable poly (ester) is at least one member selected from a group consisting of hydroxyl/carboxyl end-functionalized linear and star shaped PCL, poly(lactide), poly(glycolide), poly(lactide-co-glycolide), poly(3-hydroxybutyrate) poly(3-hydroxyvalerate) and derivatives thereof.

In yet another embodiment, α,ω-hydroxyl end-functionalized linear PCL is obtained commercially or prepared by ring opening polymerization of ε-caprolactone initiated with a glycol in the bulk at 150° C. using a catalyst.

In yet another embodiment, hydroxyl end-functionalized star-shaped PCL is prepared by ring-opening polymerization of ε-caprolactone initiated with polyol in the bulk at 150° C. using a catalyst.

In a still further embodiment, the glycol is at least one member selected from a group consisting diethylene glycol; triethylene glycol; 1,4-butanediol; 1,6-hexanediol or mixtures thereof. The polyol may be selected from, but not limited to, a group consisting of 3,3,3-tri(hydroxymethyl) propane and tetra(hydroxymethyl)methane.

In another embodiment, the catalyst may be at least one member which is selected from a group consisting of stannous 2-ethyl hexanoate, dibutyltin dilauryate, aluminum triisopropoxide.

In another embodiment, the macromolecular biodegradable chain-transfer agent may be prepared by conjugating a disulfide containing aliphatic compound to a hydroxyl/carboxyl end-functionalized biodegradable polymer and subjecting the conjugate to disulfide bond reduction in the presence of a reducing agent.

In another embodiment, the disulfide containing aliphatic compound may be at least one member selected from a group consisting 3,3'-dithiobis(propionic acid), 4,4'-dithiobis(butyric acid), 2-hydroxyethyl disulfide, and 3-hydroxypropyl disulfide, while the reducing agent may be at least one member which is selected from a group consisting of 2-mercaptoethanol, ethanedithiol, dithiothreitol, and dithioerythritol.

In another embodiment, a linear chain transfer agent $\alpha,\omega$-PCL dithiol, for the preparation of A-B-A triblock copolymers, is prepared by conjugating 3,3'-dithiobis(propionic acid) to $\alpha,\omega$-PCL diol and reducing the disulfide linkage in the conjugate.

In another embodiment, a star-shaped PCL thiol chain-transfer agent for the preparation of star-shaped block copolymers is prepared by conjugating 3,3'-dithiobis(propionic acid) to hydroxyl end-functionalized star-shaped poly($\epsilon$-caprolactone) and reducing the disulfide linkage in the conjugate.

In another embodiment, macromolecular, biodegradable chain transfer agent based on poly(D,L-lactide) is synthesized by initiating polymerization of D,L-lactide, by an aliphatic disulfide containing diol and reducing the disulfide linkages in the resulting polymers.

In another embodiment, aliphatic disulfide containing diol for initiating polymerization of D,L-lactide is selected from a group consisting 2-hydroxyethyl disulfide, 3-hydroxypropyl disulfide, 6-hydroxyhexyl disulfide etc.

In another embodiment, PHPMA-b-PCL-b-PHPMA and star-shaped PCL-b-PHPMA are prepared by free radical polymerization of N-(2-hydroxypropyl)methacrylamide in the presence of $\alpha,\omega$-PCL dithiol and star-shaped PCL thiol, respectively.

In another embodiment, PVP-b-PCL-b-PVP is prepared by free radical polymerization of N-vinyl-2-pyrrolidinone in the presence of $\alpha,\omega$-PCL dithiol.

In an another embodiment, diblock poly(D,L-lactide)-block-poly(N-vinylpyrrolidone)(PDLLA-b-PVP) is prepared by free radical polymerization of N-vinyl-2-pyrrolidinone in the presence of thiol-end functionalized poly(D,L-lactide).

In another embodiment, vinyl segments in diblock, triblock and star block copolymers can be prepared via free radical copolymerization of vinyl monomer and hydroxyl, amine functional vinyl monomer.

In another embodiment, targeting moieties e.g. folic acid, sugars, and antibodies can be conjugated to the pendant functional groups in diblock, triblock and star block copolymers prepared by the process of the instant invention.

For example, at least one targeting moiety may be conjugated to a pendant functional groups in a vinyl polymer segment, said targeting moiety being at least one member selected from the group consisting of vitamins, sugars, antibodies, lectins, peptides and combinations thereof.

In another embodiment, other vinyl monomers such as N-isopropylacrylamide, monomethoxyPEG methacrylate, methacrylic acid, acrylic acid, 2-(aminoethyl)methacrylate, 3-(aminopropyl)methacylamide hydrochloride, N,N-dimethylaminoethylmethacrylate can be polymerized individually or in combination with one another, in the presence of a macromolecular biodegradable chain-transfer agent to obtain diblock, triblock or star-shaped block copolymers.

In another embodiment, pharmaceutical compositions are prepared by including drugs (alternatively referred to as therapeutic agents with the diblock, triblock or star-shaped block copolymers. Preferably, the therapeutic agents used in accordance with the invention are hydrophobic (poorly-water soluble) or show specific interactions with the hydrophobic block. Suitable drugs include but are not limited to hydrophobic antitumor compounds (e.g. phthalocyanines, doxorubicin, vinblastine, paclitaxel, docetaxel, melphalan, teniposide, etiposide), antivirals drugs (e.g. HIV-1 protease inhibitors), immunomodulators (e.g. cyclosporin, tacrolimus), antifungals (e.g. amphotericin B, ketoconazole), central nervous system agents (e.g. anesthetics), steroidal (e.g. dexamethasone) and non-steroidal drugs (e.g., indomethacin). The pharmaceutical compositions of the present invention form nanodispersions or water-soluble supramolecular aggregates (i.e. micelles) in aqueous media. The drug nanodispersions or micelles can be prepared by means of chemical conjugation, by physical entrapment through dialysis, emulsification techniques, simple equilibration of the drug and micelles in an aqueous medium or solubilization of a drug/polymer solid dispersion in water. In addition, nanodispersions may be produced in accordance with a process as set forth in copending application having Express Mail No. EU001993104US, the contents of which are herein incorporated by reference. Said copending application is directed toward a process for the production of a sterile, stabilized nanodispersion or loaded micelle comprising a polymer and a biologically active composition; particularly to nanodispersions produced by rehydration of a freeze-dried cake produced via the direct lyophilization of a stabilized solution comprising a polymer, such as an amphiphilic block copolymer or a small molecular weight surfactant, a biologically active agent, an optional additive, and a suitable solvent.

The present invention will be further understood by the following examples, which are provided for illustration and are not construed as limiting the invention.

EXAMPLES

Materials 3,3'-Dithiobis (propionic acid) (DTPA), poly($\epsilon$-caprolactone) diol (HO-PCL-OH) ($M_n$ ca 2,000), dicyclohexyl carbodiimide (DCC), N,N-dimethylaminopyridine (DMAP), dithiothreitol (DTT), pentaerythritol, stannous 2-ethyl hexanoate, N-vinyl-2-pyrrolidinone (VP), 2,2'-azobisisobutyronitrile (AIBN), D,L-lactide, 2-hydroxyethyl disulfide, pyrene, THF, N,N-dimethylformamide (DMF), N,N-dimethylacetamide (DMAC), and dichloromethane (DCM) were purchased from Aldrich Chemical Company Inc. (Oakville, ON, Canada). N-(2-hydroxypropyl)methacrylamide (HPMA) was obtained from Polysciences Inc. (Warrington, Pa.). Amphotericin B, indomethacin and doxorubicin were procured from Sigma (Oakville, ON, Canada). Spectra/Por™ dialysis membranes of 6,000–8,000 molecular weight cut-off were from Spectrum Laboratories (Rancho Dominguez, Calif.). VP was passed through a silica gel column to remove the inhibitor sodium hydroxide. AIBN was recrystallized from ethanol. THF was freshly distilled over sodium and benzophenone before use. All other chemicals were used as received.

Characterization Methods $^1$H NMR spectroscopy: $^1$H NMR spectra of all the compounds synthesized in this work were obtained on a Bruker (Milton, ON, Canada) spectrometer operating at 300 MHz.

Molecular weight measurements: Weight—($M_w$) and number—($M_n$) average molecular weights of polymers were determined by gel permeation chromatography (GPC) on Waters Alliance GPCV 2000 chromatograph (Waters, Milford, Mass.) equipped with differential refractive index detector and the Millennium software program, under the following conditions. Three columns HT1, HT2 and HT3 with a very high to low molecular weight separation range were used in series. Polymer samples were dissolved in DMF (4 mg/mL) and injected in the system. The mobile phase was DMF containing 50 mM LiBr. Flow rate and temperature were set at 0.8 mL/min and 40° C., respectively. Molecular weights by relative analysis were obtained from comparison of the retention times of synthesized triblock copolymers with those of PEG standards.

Size measurements: Aggregate size in aqueous solutions was measured by dynamic light scattering at a 90° angle to the incident beam and at 20° C. on a Coulter N4 Plus particle size analyzer (Coulter, Miami, Fla.) equipped with software for differential size distribution intensity analysis. The aqueous solution of polymer (0.03 to 1 mg/mL) was passed through 0.22 μm filter before size measurement.

Fluorescence spectroscopy: The apparent critical aggregation concentration (CAC) of the polymers was estimated by a steady-state pyrene fluorescence method, which is based on the shift in the (0,0) band of pyrene in the excitation spectra from 333 nm to 336 nm due to its incorporation in the hydrophobic core of the micelles (Lee, S. C.; Chang, Y.; Yoon, J.-S.; Kim, C.; Kwon, I. C.; Kim, Y-H; Jeong, S. Y. 1999, *Macromolecules* 32, 1847–1852). Two mL aqueous solution of pyrene ($2*10^{-7}$ M) was added to a 2 mL polymer solution with increasing concentrations (0.015–5,000 mg/L). These solutions were kept at 4° C. in the dark and stirred gently for 16 h. Their excitation spectra were recorded on an AMINCO Bowman Series 2 luminescence spectrometer (Thermo Spectronic, Rochester, N.Y.) at $\lambda_{ex}$=336 nm (bandpass 1 nm) and $\lambda_{em}$=393 nm (bandpass 4 nm). The CAC was determined from the intersection of 2 straight lines (the horizontal line with an almost constant value of the ratio $I_{336\ nm}/I_{333\ nm}$ and the vertical line with a steady increase in the ratio value) on the graph of the fluorescence intensity ratio $I_{336\ nm}/I_{333\ nm}$ vs. log polymer concentration.

Example 1

Synthesis of α,ω-poly(ε-caprolactone)-dithiol: chain-transfer Agent for the Preparation of A-B-A Triblock Copolymers Step 1: Synthesis of α,ω-poly(ε-caprolactone)-di(3,3'-dithiobis(propionate)) (DTPA-PCL-DTPA)

Two g of HO-PCL-OH (1 mmol) and 1 g of DTPA (5 mmol) were added to 10 mL THF. The reaction mixture was stirred to obtain a clear solution. To this, 0.8 g DCC (4 mmol) and 20 mg DMAP dissolved in 5 mL THF was added in one portion. The reaction mixture was stirred at room temperature for 2 days. It was filtered to remove dicyclohexyl urea (DCU). The clear solution was concentrated in vacuo. One hundred mL DCM was then added and allowed to stand for 1 h to precipitate the remaining traces of DCU. The DCM solution was filtered and extracted with 3×50 mL 5% aq. NaCl. The organic layer was dried on anhydrous magnesium sulphate. DCM was evaporated under reduced pressure to isolate DTPA-PCL-DTPA. The product was dried in vacuo for 16 h. Yield (90%).

$^1$H NMR (CDCl$_3$): 4.17 δ, s, 4H (terminal —CH$_2$—O—CO— of PCL); 4.00 δ, s, 27H (—CH$_2$—O—CO— of PCL main chain); 3.64 δ, s, 3.6H (—CH$_2$—COOH of DTPA); 2.87 δ, d, 7H (—CH$_2$—S—S—CH$_2$— of DTPA); 2.72 δ, m, 8H (—O—CH$_2$—CH$_2$—O— of PCL diethylene glycol); 2.25 δ, s, 27H (—CH$_2$—CO— of PCL carbonyl+ DTPA carbonyl); 1.59 δ, s, 59H (—CH$_2$— of PCL methylene groups); 1.32 δ, s, 29H (—CH$_2$— of PCL methylene groups).

Step 2: Reduction of DTPA-PCL-DTPA to HS-PCL-SH.

Two g of DTPA-PCL-DTPA was dissolved in 10 mL DMF. DTT (0.616 g, 2.5 times molar excess over disulfide groups) was added and the reaction mixture was stirred at room temperature for 24 h. The DMF solution was poured in cold water (1 L) under stirring to precipitate HS-PCL-SH. The product was isolated by filtration, washed thoroughly with water and dried in vacuo. Yield (43%). $^1$H NMR (CDCl$_3$): 4.19 δ, s, 4H (terminal —CH$_2$—O—CO of PCL); 4.02 δ, t, 38H (—CH$_2$—O—CO— of PCL main chain); 3.6 δ, s, 4.25H (HS—CH$_2$—CH$_2$—CO— of DTPA); 2.88 δ, m, 4.27H (HS—CH$_2$—CH$_2$—CO— of DTPA); 2.7–2.72 δ, m, 8H (—O—CH$_2$—CH$_2$—O— of PCL diethylene glycol); 2.27 δ, t, 40H (—CH$_2$—CO— of PCL carbonyl); 1.61 δ, s, 79H (—CH$_2$— of PCL methylene groups); 1.34 δ, d, 43H (—CH$_2$— of PCL methylene groups).

Example 2

Synthesis of poly(N-(2-hydroxypropyl)methacrylamide)-block-poly(ε-caprolactone)-block-poly(N-2-hydroxypropyl-methacrylamide) (PHPMA-b-PCL-b-PHPMA)

A typical procedure for PHPMA-b-PCL-b-PHPMA (1:0.33) is described below (the numbers in brackets represent the molar feed ratio HPMA: caprolactone (CL)). In a 3-neck round bottom flask equipped with a magnetic stirring bar and reflux condenser, HS-PCL-SH (0.80 g, 0.36 mmol), HPMA (3 g, 20.9 mmol) and AIBN (0.034 g, 0.209 mmol) were dissolved in DMF (10 mL). The solution was purged with nitrogen for 30 min at room temperature and the flask was immersed in an oil bath preheated to 80° C. Polymerization proceeded for 16 h under continuous nitrogen purging. The DMF solution was poured in diethyl ether (800 mL) to precipitate the polymer, which was dissolved in 100 mL water and dialyzed against 2 L water at 4° C. for 2 days. The water was replaced every 12 h. The aqueous polymer solution was centrifuged at 4,000 g for 5 min to separate any unreacted HS-PCL-SH (very small amount observed). Then, the solution was decanted, filtered through 0.45-μm filter and lyophilized to obtain PHPMA-b-PCL-b-PHPMA. Yield: 2.5 g (65%). Typical $^1$H NMR (DMSO d$_6$) spectral data are: 4.64 δ, s, (—CH—OH of PHPMA); 4.03 δ, s, (terminal —CH$_2$—O—CO— of PCL); 3.90 δ, t, (—CH$_2$—O—CO— of PCL main chain); 3.59 δ, s, (—NH— of PHPMA); 2.81 δ, s, (HO(CH)—CH$_2$—NH— of PHPMA); 2.19 δ, t, (—CH$_2$—CO— of PCL); 1.44 δ, m, (—CH$_2$— backbone of PHPMA+PCL methylene groups); 1.21 δ, d, (PCL methylene groups); 0.73–0.94 δ, d, (—CH$_3$— of PHPMA backbone+pendant —CH$_3$ of PHPMA).

Ellman's test for detection of free —SH groups performed on the polymer. The test was negative, indicating complete utilization of thiol groups of HS-PCL-SH in chain-transfer to PHPMA and the formation of the triblock copolymer. Polymers with different molar feed ratio of HPMA: CL were synthesized according to the process described in example 2. Yields (60–70%). Polymer characterization data are listed in Table 1 (entries 1–4).

purification were in the range of 50–60%. These polymers also exhibited negative Ellman's test for free —SH group indicating complete utilization of thiol groups in HS-PCL-SH in chain-transfer to PVP and formation of the triblock copolymer. Polymer characterization data are listed in Table 1 (entries 5–7).

TABLE 1

Molecular weights, composition and micellar characterization data for A-B-A triblock copolymers

| Entry No. | Polymer[1] | CL/HPMA or VP molar ratio in purified product[2] | $M_w$[3] | $M_n$[3] | $M_w/M_n$ | $M_n$ by $^1$H NMR[4] | CAC[5] (mg/L) | $K_v * 10^5$ | Micelle size[6] (nm) |
|---|---|---|---|---|---|---|---|---|---|
| 1 | PHPMA-b-PCL-b-PHPMA (1:0.25) | 0.20 | 12,100 | 6,700 | 1.80 | 14,700 | 3.8 ± 0.8 | 2.6 ± 0.3 | 36 ± 7 (62%), 154 ± 87 (38%) |
| 2 | PHPMA-b-PCL-b-PHPMA (1:0.33) | 0.22 | 10,700 | 6,100 | 1.75 | 13,400 | 3.5 ± 1 | 2.6 ± 0.2 | 34 ± 2 (58%), 100 ± 11 (42%) |
| 3 | PHPMA-b-PCL-b-PHPMA (1:0.51) | 0.35 | 7,700 | 4,800 | 1.60 | 9,100 | 2 ± 0.1 | 2.5 ± 0.3 | 31 ± 1 (80%), 147 ± 36 (20%) |
| 4 | PHPMA-b-PCL-b-PHPMA (1:0.96) | 0.90 | 5,600 | 3,600 | 1.55 | 4,700 | 1.3 ± 0.2 | 2.3 ± 0.2 | 37 ± 10 (20%), 220 ± 70 (80%) |
| 5 | PVP-b-PCL-b-PVP (1:0.20) | 0.17 | 13,300 | 4,600 | 2.89 | 13,700 | 3 ± 1 | 3.8 ± 0.2 | 51 ± 1 (15%), 198 ± 24 (85%) |
| 6 | PVP-b-PCL-b-PVP (1:0.26) | 0.20 | 13,400 | 4,600 | 2.91 | 11,400 | 1.8 ± 1 | 4.2 ± 0.6 | <3 (29%), 47 ± 1 (41%), 245 ± 50 (30%) |
| 7 | PVP-b-PCL-b-PVP (1:0.40) | 0.26 | 6,200 | 3,100 | 2.0 | 9,500 | 2 ± 0.5 | 3.2 ± 0.5 | 47 ± 10 (20%), 186 ± 28 (80%) |

[1]Numbers in the parentheses represent molar feed ratios of monomer:CL.
[2]Determined by $^1$H NMR from the ratio of the number of protons under the peaks characteristic of HPMA or VP and PCL, respectively.
[3]Determined by GPC using PEG standards.
[4]Calculated from the number of protons under the peaks characteristic of HPMA or VP. The average $M_n$ of PCL was assumed to be 2,000.
[5]The value is the average of 2 experiments.
[6]Measured by dynamic light scattering using aqueous polymer solutions at 1 mg/mL. The values reported are the average of 3 measurements. Numbers in the parentheses represent the percentage population of micelles of a particular size.

Example 3

Synthesis of poly(N-vinylpyrrolidone)-block-poly(ε-caprolactone)-block-poly(N-vinylpyrrolidone) (PVP-b-PCL-b-PVP)

These polymers were synthesized with increasing molar feed ratio of CL to VP, following the procedure described for PHPMA-b-PCL-b-PHPMA. Typical $^1$H NMR (DMSO $d_6$) spectral data are: 4.10 δ, s, (terminal —CH$_2$—O—CO— of PCL); 3.97 δ, s, (—CH$_2$—O—CO— of PCL main chain); 3.59–3.74 δ, d, (—CH— of PVP backbone); 3.14 δ, s, (—CH$_2$— of PVP backbone); 1.28–2.26 δ, m, (—CH$_2$ of pyrrolidone ring+PCL methylene groups). Polymer yields after

Example 4

Drug Loading in A-B-A Triblock Copolymer Micelles

An illustrative, albeit non-limiting procedure for loading a drug, e.g. an anticancer drug e.g. doxorubicin and antifungal drug e.g. amphotericin B is described below.

Five mg of doxorubicin or 5 mg of amphotericin B and 50 mg of PHPMA-b-PCL-b-PHPMA were dissolved in 5 mL DMAC. Four-fold molar excess of triethylamine over the drug was added. The clear solution of polymer and drug was allowed to stand at room temperature for 30 min. Then, 0.5 mL water was added in portions of 0.1 mL. This solution was placed in a dialysis membrane bag of 6,000–8,000 molecular weight cut-off and dialyzed against 2 L water for 24 h at room temperature. The water in the outer chamber was replaced every 12 h. The solution in the dialysis bag was passed through 0.22-μm filters and lyophilized to obtain drug-loaded micelles. Drug-loading was estimated by spectrophotometry after dissolving the micelles in DMAC and measuring the absorbance at 486 and 412 nm for doxorubicin and amphotericin B, respectively. Similar procedure was followed to load doxorubicin and amphotericin B in PVP-b-PCL-b-PVP micelles. Drug loading data are listed in Table 2.

TABLE 2

Drug loading data for A-B-A triblock copolymer by the dialysis method

| Entry No. | Polymer | Initial drug loading (w/w %)[1] | | Drug loading after dialysis (w/w %)[1] | | Entrapment efficiency (%) | |
|---|---|---|---|---|---|---|---|
| | | Doxorubicin | Amphotericin B | Doxorubicin | Amphotericin B | Doxorubicin | Amphotericin B |
| 1 | PHPMA-b-PCL-b-PHPMA (1:0.25) | 9 | 16.6 | 1.9 | 0.323 | 21.1 | 1.9 |
| 2 | PHPMA-b-PCL-b-PHPMA (1:0.33) | 9 | 16.6 | 2.4 | 1.58 | 26.6 | 9.51 |
| 3 | PHPMA-b-PCL-b-PHPMA (1:0.51) | 9 | 16.6 | 1.5 | 1.91 | 16.6 | 11.50 |
| 4 | PHPMA-b-PCL-b-PHPMA (1:0.96) | 9 | 16.6 | 1.1 | ND[2] | 12.2 | ND[2] |
| 5 | PVP-b-PCL-b-PVP (1:0.20) | 9 | 16.6 | 0.84 | 1.00 | 9.3 | 6.04 |
| 6 | PVP-b-PCL-b-PVP (1:0.26) | 9 | 16.6 | 1.1 | 0.91 | 12.2 | 5.51 |
| 7 | PVP-b-PCL-b-PVP (1:0.40) | 9 | 16.6 | 1.59 | 3.89 | 17.6 | 23.43 |

[1]Drug loading based on w/w drug/(polymer + drug).
[2]Not detectable.

Example 5

Synthesis of Star-poly(ε-caprolactone)-tetrakis-thiol thiol (Star-PCL-(SH)$_4$): Chain-transfer Agent for the Preparation of Star-shaped Block Copolymers Step 1: Synthesis of Star-shaped poly(ε-caprolactone) ((Star-PCL))

Two 9 of ε-caprolactone (mmol), 0.03 9 of pentaerythritol (mmol), 0.025 g of stannous 2-ethyl hexanoate (mmol) were place in a Schlenk polymerization tube equipped with a magnetic stirring bar. Vacuum was applied to the tube for 10 minutes. Then the tube was filled with nitrogen. This was repeated three times. Finally the tube was closed under vacuum and immersed in an oil bath preheated to 150° C. Polymerization was allowed to proceed for 16 h under stirring. Polymerization tube was cooled to room temperature. The polymer was dissolved in 20 mL dichloromethane and reprecipitated in n-hexane. The polymer was isolated by filtration and dried in vacuum for 16 h. Yield (85%). $^1$H NMR (CDCl$_3$): 4.10 δ s, 8H (—C$\underline{H}_2$—O—CO— of pentaerythritol), 4.05 δ, t, 192H (—C$\underline{H}_2$—O—CO— of PCL), 3.64 δ, t, 8H (terminal —C$\underline{H}_2$—OH of PCL arms), 2.30 δ, t, 192H (—C$\underline{H}_2$—CO— of PCL carbonyl); 1.61 δ, m, 424H (—C$\underline{H}_2$— of PCL methylene groups); 1.34 δ, d, 200H (—C$\underline{H}_2$— of PCL methylene groups).

Step 2: Synthesis of star-poly(ε-caprolactone)-tetrakis(3,3'-dithiobis(propionate)) ((star-PCL-(DTPA)$_4$)

1.5 g of star-PCL (0.54 mmol —OH) and 0.6 g of DTPA (2.7 mmol, 5 fold excess over —OH groups) were dissolved in 15 mL THF. To this, 0.5 g of DCC (2.18 mmol, 4 fold excess over —OH groups) and 100 mg DMAP in 10 mL THF was added in one portion. The reaction mixture was stirred at room temperature for 2 days. It was filtered to remove DCU salt. THF solution was concentrated in vacuum. The viscous liquid which was obtained, dissolved in 100 mL DCM and allowed to stand for 1.5 h to precipitate remaining traces of DCU. The clear solution was concentrated to isolate the product which was dried in vacuum for 16 h. Yield 1 g (58%). $^1$H NMR (CDCl$_3$): 4.09 δ s, 8H (—C$\underline{H}_2$—O—CO— of pentaerythritol), 4.05 δ, t, 129H (—C$\underline{H}_2$—O—CO— of PCL), 2.92 δ, m, 24H (8H of terminal —C$\underline{H}_2$—OH of PCL arms+16H of —C$\underline{H}_2$—CO— of DTPA), 2.72 δ, m, 17H (—C$\underline{H}_2$—S— of DTPA), 2.29 δ, t, 135H (—C$\underline{H}_2$—CO— of PCL carbonyl); 1.64 δ, m, 316H (—C$\underline{H}_2$— of PCL methylene groups); 1.37 δ, d, 167H (—C$\underline{H}_2$— of PCL methylene groups).

Step 3: Reduction of Star-PCL-(DTPA)$_4$ to Star-PCL-(SH)$_4$ 0.5 g star-PCL-(DTPA)$_4$ was dissolved in 5 mL DMF. One hundred mg dithiothreitol (3.6 fold molar excess over disulfide groups) was added to the solution and stirred at room temperature for 24 h. The solution was poured in 1 L cold water to precipitate star-PCL-(SH)$_4$. The product was isolated by filtration washed thoroughly with water and dried in vacuum for 2 h. The product was stored at −20° C. till further use. Yield (80%). $^1$H NMR (CDCl$_3$): 4.11 δ s, 8H (—C$\underline{H}_2$—O—CO— of pentaerythritol), 4.06 δ, t, 150H (—C$\underline{H}_2$—O—CO— of PCL+terminal —C$\underline{H}_2$—O-DTPA), 2.94 δ, t, 9H (—C$\underline{H}_2$—CO— of DTPA), 2.77 δ, m, 10H (—C$\underline{H}_2$—S— of DTPA), 2.31 δ, t, 135H (—CH$_2$—CO— of PCL carbonyl); 1.64 δ, m, 333H (—C$\underline{H}_2$— of PCL methylene groups); 1.37 δ, m, 189H (—C$\underline{H}_2$— of PCL methylene groups).

Example 6

Synthesis of star-shaped poly(ε-caprolactone)-block-poly(N-(2-hydroxypropyl)methacrylamide)

In a 3-neck round bottom flask equipped with a magnetic stirring bar and reflux condenser, 0.1 g star-PCL-(SH)$_4$, 1 g HPMA (6.9 mmol), 0.011 g AIBN (0.069 mmol) were dissolved in 10 mL DMF. The solution was purged with nitrogen for 30 min at room temperature and the flask was immersed in an oil bath preheated to 80° C. Polymerization proceeded for 16 h under continuous nitrogen purging. The DMF solution was poured in diethyl ether (800 mL) to precipitate the polymer, which was dissolved in 100 mL water and dialyzed against 2 L water at 4° C. for 2 days. The water was replaced every 12 h. The aqueous polymer solution was centrifuged at 4,000 g for 5 min to separate any unreacted star-PCL-(SH)$_4$ (very small amount observed). Then, the solution was decanted, filtered through 0.45-μm filter and lyophilized to obtain star-shaped PCL-b-PHPMA. Yield (72%). Typical $^1$H NMR (DMSO d$_6$) spectral data are: 4.69 δ, s, (—CH—OH of PHPMA); 4.03 δ, s, (—CH$_2$—O—CO— of pentaerythritol); 3.95 δ, t, (—CH$_2$—O—CO— of PCL main chain); 3.65 δ, s, (—NH— of PHPMA); 2.89 δ, s, (HO(CH)—CH$_2$—NH— of PHPMA); 2.24 δ, t, (—CH$_2$—CO— of PCL); 1.50 δ, m, (—CH$_2$— backbone of PHPMA+PCL methylene groups); 1.26 δ, d, (PCL methylene groups); 0.79–1.00 δ, d, (—CH$_3$— of PHPMA backbone+pendant —CH$_3$ of PHPMA).

Ellman's test for detection of free —SH groups was performed on the polymer. The test was negative, indicating complete utilization of thiol groups of (star-PCL-(SH)$_4$ in chain-transfer to PHPMA and the formation of the star block copolymer. Polymers with different molar feed ratio of HPMA: CL were synthesized according to the process described in example 6. Yields were 60–70%. Polymer characterization data are listed in Table 3.

in the outer chamber was replaced every 12 h. The solution in the dialysis bag was passed through 0.22-μm filters and lyophilised to obtain drug-loaded micelles. Drug-loading was estimated by spectrophotometry after dissolving the micelles in DMF and measuring the absorbance at 320 nm. Drug loading data are shown in Table 4.

TABLE 4

Drug loading data for Star-block copolymers

| Entry No. | Polymer | Initial indomethacin loading w/w %)[1] | Indomethacin loading after dialysis (w/w %)[1] | Entrapment efficiency (%) |
|---|---|---|---|---|
| 1 | Star-PCL-b-PHPMA (0.08:1) | 28.5 | 5.08 | 17.8 |
| 2 | Star-PCL-b-PHPMA (0.12:1) | 28.5 | 5.68 | 19.9 |
| 3 | Star-PCL-b-PHPMA (0.15:1) | 28.5 | 9.9 | 35 |
| 4 | Star-PCL-b-PHPMA (0.20:1) | 28.5 | 12.5 | 43.8 |

[1]Drug loading based on w/w drug/(polymer + drug).

TABLE 3

Molecular weights, composition and micellar characterization data for star-shaped bock copolymers

| Entry No. | Polymer[1] | CL/HPMA molar ratio in purified product[2] | M$_n$ by $^1$H NMR[3] | CAC[4] (mg/L) | K$_v$*10$^5$ | Micelle size[5] (nm) 0.2% w/w | Micelle size[5] (nm) 0.03% w/w |
|---|---|---|---|---|---|---|---|
| 1 | Star-PCL-b-PHPMA (0.08:1) | 0.09 | 93,700 | 1.8 ± 0.4 | 8.1 ± 0.7 | 110 ± 10 | 110 ± 10 (75%), 1 (25%) |
| 2 | Star-PCL-b-PHPMA (0.12:1) | 0.15 | 87,000 | 1.4 ± 0.2 | 6.5 ± 0.7 | 100 ± 20 | 125 ± 15 (85%), 1 (15%) |
| 3 | Star-PCL-b-PHPMA (0.15:1) | 0.16 | 85,200 | 1.4 ± 0.3 | 7.8 ± 0.6 | 120 ± 10 | 120 ± 20 (85%), 1 (15%) |
| 4 | Star-PCL-b-PHPMA (0.20:1) | 0.25 | 50,300 | 1.2 ± 0.1 | 5.1 ± 0.2 | 150 ± 25 | 125 ± 15 (85%), 1 (15%) |

[1]Numbers in the parentheses represent molar feed ratios of HPMA:CL.
[2]Determined by $^1$H NMR from the ratio of the number of protons under the peaks characteristic of HPMA and PCL, respectively.
[3]Calculated from the number of protons under the peaks characteristic of HPMA & PCL.
[4]The value is the average of 2 experiments.
[5]Measured by dynamic light scattering using aqueous polymer solutions. The values reported are the average of 3 measurements. Numbers in the parentheses represent the percentage population of micelles of a particular size. 0.2% w/w polymer solution exhibited unimodal micelles.

Example 7

Drug Loading in Star-block Copolymer Micelles

Twenty mg of indomethacin and 50 mg of star-PCL-b-PHPMA were dissolved in 5 mL DMAC. The clear solution of polymer and drug was allowed to stand at room temperature for 30 min. Then, 0.5 mL water was added in portions of 0.1 mL. This solution was placed in a dialysis membrane bag of 6,000–8,000 molecular weight cut-off and dialyzed against 2 L water for 24 h at room temperature. The water Example 8

Synthesis of ω-poly(D,L-lactic acid)-thiol P(DLLA)-SH: chain-transfer agent for the preparation of diblock copolymers Step 1: Synthesis of 2,2'-dithiobis(hydroxyethyl)-poly(D,L-lactide) P(DLLA)-S-S-P(DLLA)

Three grams of D,L-lactide (20.8 mmol), 0.09 g of 2-hydroxyethyl disulfide(0.58 mmol), 0.025 g of stannous 2-ethyl hexanoate were place in a Schlenk polymerization tube equipped with a magnetic stirring bar. Vacuum was applied to the tube for 10 minutes. Then, the tube was filled with nitrogen. This was repeated three times. Finally the tube was closed under vacuum and immersed in an oil bath preheated to 150° C. Polymerization was allowed to proceed for 16 h under stirring. Polymerization tube was cooled to room temperature. The polymer was dissolved in 20 mL dichloromethane and reprecipitated in n-hexane. The polymer was isolated by filtration and dried in vacuum for 16 h. Yield (66%). $^1$H NMR (CDCl$_3$): 5.16 δ s, 64H (CH$_3$—CH—O—CO— of lactic acid)), 4.37–4.40 δ, m, 4H (—O—CH$_2$—CH$_2$—S—S— of 2-hydroxyethyl disulfide), 2.90 δ, t, 4H, (—CH$_2$—S—S— of 2-hydroxyethyl disulfide), 1.57 δ, s, 206 H (CH$_3$—CH—O—CO of lactic acid). M$_n$ ($^1$H NMR): 4600.

Step 2: Reduction of P(DLLA)-S-S-P(DLLA) to P(DLLA)-SH

Two g P(DLLA)-S-S-P(DLLA) was dissolved in 15 mL DMF. Five hundred and sixty mg dithiothreitol (ca. 5 fold molar excess over disulfide groups) was added to the solution and stirred at room temperature for 24 h. The solution was poured in 1 L cold water to precipitate P(DLLA)-SH. The product was isolated by filtration washed thoroughly with water and dried in vacuum for 16 h. The product was stored at −20° C. till further use. Yield (30%). $^1$H NMR (CDCl$_3$): 5.16 δ s, 40H (CH$_3$—CH—O—CO— of lactic acid) 4.37 δ, m, 2H (—O—CH$_2$—S—S— of 2-hydroxyethyl disulfide), 3.66 δ, m, 2H (—O—CH$_2$—CH$_2$—SH at P(DLLA)-SH chain end), 1.57 δ, s, 127H (CH$_3$—CH—O—CO of lactic acid). M$_n$ ($^1$H NMR): 2880.

Example 9

Preparation of poly(D,L-lactide)-block-poly(N-vinyl pyrrolidone) P(DLLA)-b-PVP

In a 3-neck round bottom flask equipped with a magnetic stirring bar and reflux condenser, 0.2 g P(DLLA)-SH, 1 g VP (9 mmol), 0.015 g AIBN (0.09 mmol) were dissolved in 10 mL DMF. The solution was purged with nitrogen for 30 min at room temperature and the flask was immersed in an oil bath preheated to 80° C. Polymerization proceeded for 6 h under continuous nitrogen purging. The DMF solution was poured in diethyl ether (800 mL) to precipitate the polymer. Yield (50%). $^1$H NMR (CDCl$_3$): 5.16 δ s, 40H (CH$_3$—CH—O—CO— of lactic acid)), 3.72 δ, s, 277H (—CH—CH$_2$— of PVP backbone), 3.21 δ, s, 535H (—CH—CH$_2$— of PVP backbone), 2.35–1.47 δ, m, 1743H(—CH$_2$— of pyrrolidone ring), 1.5 δ (CH$_3$ of lactide). M$_n$ ($^1$H NMR): 33,600. PDLLA incorporation: 8.5% w/w (50% of the feed amount). Ellman's test was negative for P(DLLA)-PVP.

All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures. One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A therapeutic composition consisting of:
   an amphiphilic diblock, triblock or star-shaped block copolymer formed by a biodegradable polymer selected from the group consisting of a polyester, a polyamide, a poly(ester-amide), a polyanhydride and combinations thereof, being covalently attached at the polymer ends to at least one hydrophilic vinyl polymer by way of a divalent sulfur atom; and
   an effective amount of at least one therapeutic agent;
   wherein said therapeutic composition is characterized by its ability to form a nanodispersion or micelle in aqueous media.

2. The therapeutic composition accordance with claim 1 wherein said hydrophilic vinyl polymer is at least one member selected from the group consisting of poly(N-2-hydroxypropylmethacrylamide), poly(N-vinylpyrrolidone), poly(ethylene glycol)methacrylate, poly(N-isopropyl acrylamide), polyacrylic acid, polymethacrylic acid, poly(2-aminoethylmethacrylate), poly(3-aminopropylmethacrylamide), poly(2-N,N-dimethylaminoethylmethacrylate) and copolymers thereof.

3. A therapeutic composition consisting of:
   an amphiphilic diblock, triblock or star-shaped block copolymer formed by a biodegradable polymer selected from the group consisting of a polyester, a polyamide, a poly(ester-amide), a polyanhydride and combinations thereof, being covalently attached at the polymer ends to at least one hydrophilic vinyl polymer by way of a divalent sulfur atom;
   and an effective amount of at least one therapeutic agent; and at least one targeting moiety conjugated to pendant functional groups in said at least one hydrophilic vinyl polymer;
   wherein said therapeutic composition is characterized by its ability to form a nanodispersion or micelle in aqueous media.

4. The therapeutic composition accordance with claim 3 wherein said targeting moiety is at least one member selected from the group consisting of vitamins, sugars, antibodies, lectins, peptides and combinations thereof.

5. The therapeutic composition in accordance with claim 1 wherein:
   said at least one therapeutic agent is poorly water-soluble and is at least one member selected from the group consisting of anticancer drugs, antifungal drugs, antiviral drugs, antibacterials, immunomodulators, central nervous system agents, anti-inflammatory drugs, or combinations thereof.

6. The therapeutic composition in accordance with claim 5 wherein:
   said anticancer drug is at least one member selected from the group consisting of aluminium chloride phthalocyanines, doxorubicin, vinblastine, paclitaxel, docetaxel, melphalan, teniposide, etiposide, and combinations thereof.

7. The therapeutic composition in accordance with claim 3 wherein said targeting moiety is provided in an amount effective to provide site-specific delivery of said therapeutic agent.

8. The therapeutic composition accordance with claim 1 wherein said biodegradable polyester is at least one member selected from the group consisting of hydroxyl or carboxyl end-functionalized linear and star shaped poly($\epsilon$-caprolactone), poly(L-lactide), poly(D-lactide), poly(D,L-lactide), poly(glycolic acid), poly(lactide-co-glycolide), poly(3-hydroxybutyrate) and derivatives thereof.

* * * * *